(12) United States Patent
Yu et al.

(10) Patent No.: US 11,259,846 B1
(45) Date of Patent: Mar. 1, 2022

(54) ROD CONNECTOR DEVICE FOR CERVICAL SPINE

(71) Applicant: Solco Biomedical Co., Ltd., Pyeongtaek-si (KR)

(72) Inventors: Hwi Geun Yu, Pyeongtaek-si (KR); Mi Rim Hyeon, Hwaseong-si (KR)

(73) Assignee: Solco Biomedical Co., Ltd., Pyeongtaek-si (KR)

( * ) Notice: Subject to any disclaimer, the term of this patent is extended or adjusted under 35 U.S.C. 154(b) by 0 days.

(21) Appl. No.: 17/105,680

(22) Filed: Nov. 27, 2020

(30) Foreign Application Priority Data

Nov. 3, 2020 (KR) .................. 10-2020-0145582

(51) Int. Cl.
*A61B 17/70* (2006.01)
(52) U.S. Cl.
CPC .................. *A61B 17/705* (2013.01)
(58) Field of Classification Search
CPC ............ A61B 17/7041; A61B 17/7043; A61B 17/7049; A61B 17/705; A61B 17/7052
See application file for complete search history.

(56) References Cited

U.S. PATENT DOCUMENTS 8,066,746 B2 * 11/2011 Glerum .............. A61B 17/7041
606/278
2018/0280062 A1 * 10/2018 Lee ...................... A61B 17/705

FOREIGN PATENT DOCUMENTS

KR 10-2008-0112851 A 12/2008

* cited by examiner

*Primary Examiner* — Lynnsy M Summitt
(74) *Attorney, Agent, or Firm* — Revolution IP, PLLC (57) ABSTRACT

A rod connector device includes a first clamp having, on one side thereof, a first grip groove and a first grip expansion groove sequentially connected to each other, a second clamp contacting the first clamp, the second clamp having, on another side thereof, a second grip groove and a second grip expansion groove sequentially connected to each other, a grip applying a binding force to a first rod and a second rod, when the first and second clamps are connected to each other so that the first and second grip expansion grooves communicate with each other, and the first and second rods are grip-secured in the first and second grip grooves.

5 Claims, 9 Drawing Sheets

ROD CONNECTOR DEVICE FOR CERVICAL SPINE

CROSS REFERENCE TO PRIOR APPLICATION

This application claims priority under 35 U.S.C. § 119 to Korean Patent Application No. 10-2020-0145582 filed on Nov. 3, 2020, in the Korean Intellectual Property Office (KIPO), the disclosure of which is incorporated by reference herein in its entirety.

BACKGROUND

Technical Field

Aspects of embodiments of the present disclosure relate to a securing device (e.g., brace or immobilizing device) for spine used in spine surgery, and more particularly, to a rod connector device connecting and securing a cervical rod, secured on a cervical spine, and a thoracic rod, secured on a thoracic spine, so that the cervical rod and the thoracic rod are extendable.

Discussion of Related Art

A cervical spine securing device (e.g., brace or immobilizing device) is used to brace or secure each cervical spine so that it does not move when treating cervical disc disease, cervical hernial disc, cervical spondylosis myelopathy, cervical fracture and dislocation, and the like.

Figure 1:
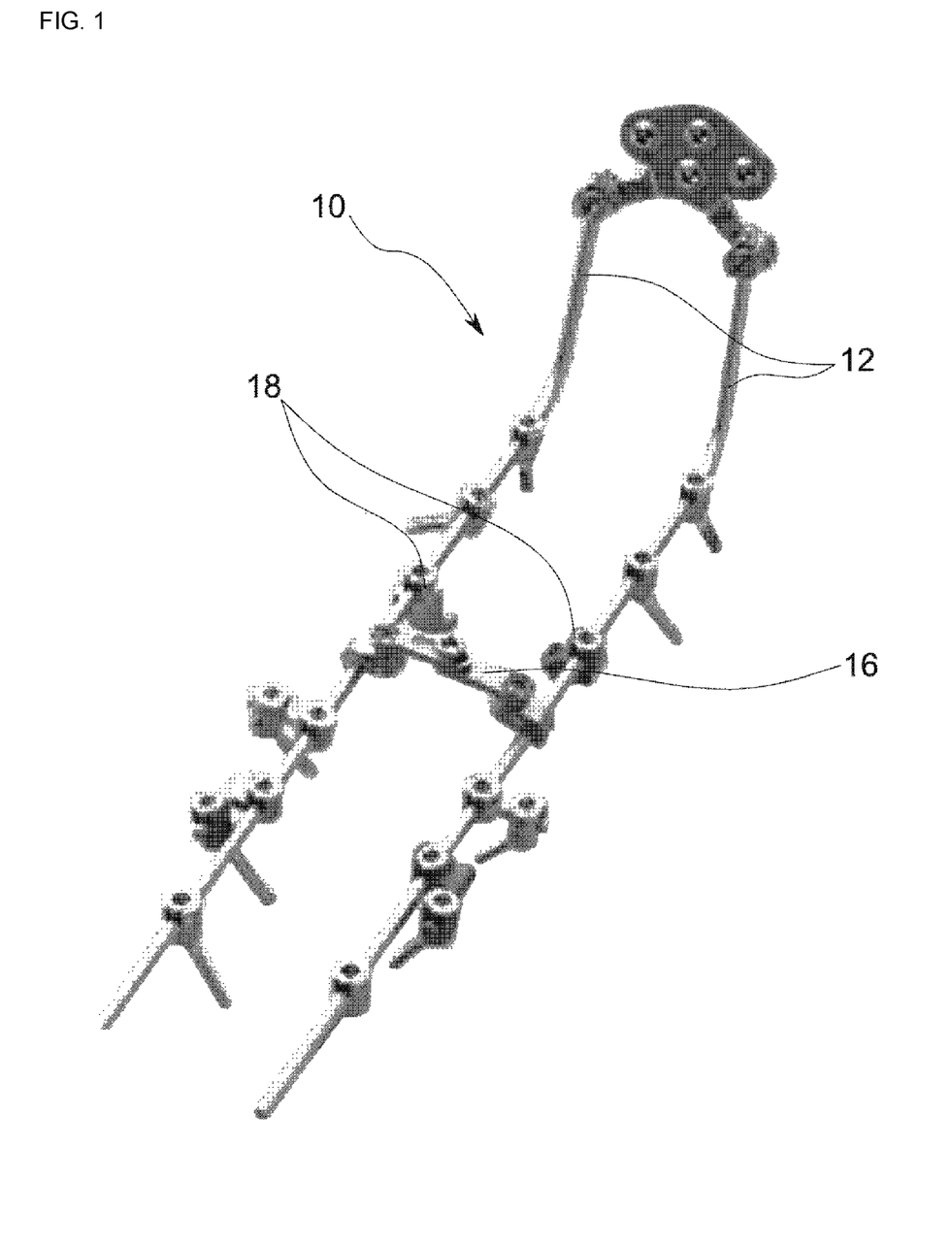
FIG. 1 is a perspective view illustrating a conventional securing device for cervical spine.

As illustrated in FIG. 1, a conventional cervical spine brace 10 includes cervical rods 12 disposed in a length direction of a cervical spine, a cross link device 16 for interconnecting the cervical rods 12, and a plurality of fastening members 18 connected to the cervical rods 12 and fastened along the cervical spine.

Figure 2:
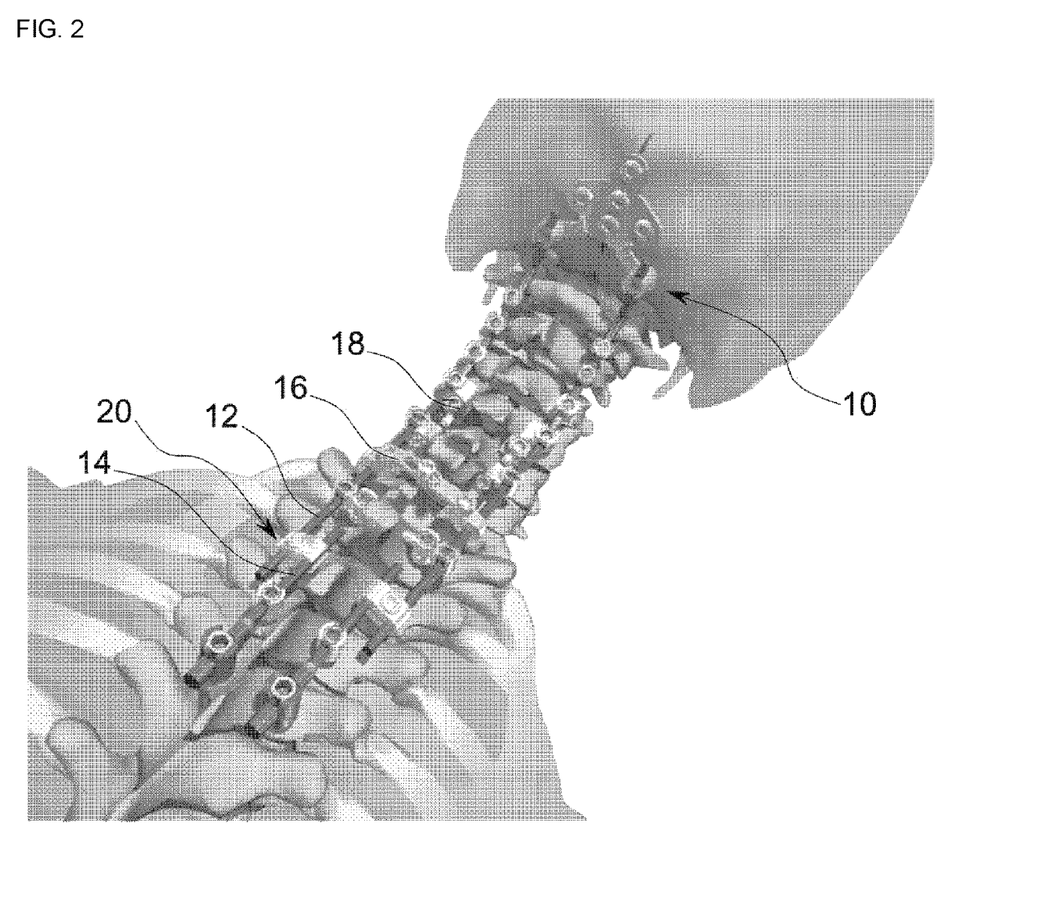
FIG. 2 is a view illustrating a state of use in which the conventional securing device for cervical spine is installed on a cervical spine.

In the cervical spine securing device 10, as illustrated in FIG. 2, a thoracic rod 14 is disposed longitudinally parallel to the cervical rod 12 so as to overlap inwardly or outwardly a lower portion of the cervical rod 12, and the rod connector 20 connects the cervical rod 12 and the thoracic rod 14 to each other.

Figure 3:
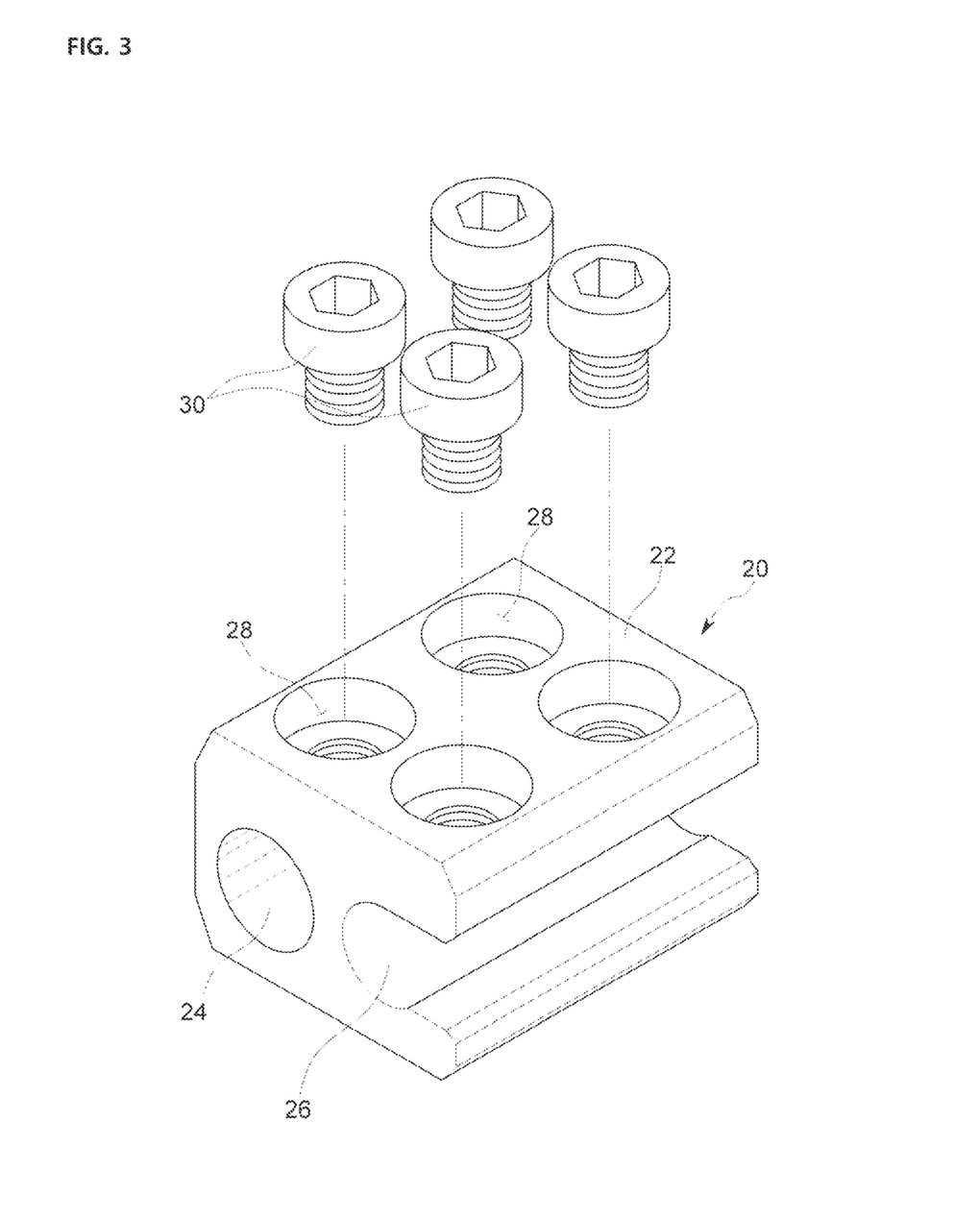
FIG. 3 is an exploded perspective view illustrating the conventional securing device for cervical spine.

A rod clamp is disclosed in Korean Patent Publication No. 10-2008-0112851 (Patent Document 1). The rod clamp 20 disclosed in Patent Document 1, as illustrated in FIG. 3, includes a body 22 in which an insertion hole 24 and an insertion hole 26 are defined in a length direction, and a plurality of fastening holes 28 communicating with the first rod insertion hole 24 and the second rod insertion hole 26 are defined on an upper surface of the body 22. A fastening 30 is fastened to the fastening hole 28 of the body 22 so as to secure first and second rods that are inserted to the insertion hole 24 and the insertion hole 26, respectively.

However, in Patent Document 1, since the rod clamp 20 secures the first and second rods respectively inserted into the insertion hole 24 and the insertion groove 26 through the use of the fastening 30, it is impossible to adjust an angle between the first and second rods.

Accordingly, in a case where the first and second rods installed on cervical spine cannot be installed in parallel, a rod clamp should be separately manufactured according to the rod position.

SUMMARY OF THE INVENTION

Embodiments of the present disclosure are directed to a rod connector device for cervical spine capable of adjusting an angle between rods, thereby making it applicable to spine or cervical spine surgery conveniently.

Embodiments of the present disclosure are further directed to a rod connector device for cervical spine that is universally applicable irrespective of the position of rods installed on the cervical spine.

According to an embodiment of the present disclosure, a rod connector device for cervical spine includes a first clamp having, on one side thereof, a first grip groove and a first grip expansion groove sequentially connected to each other, a second clamp contacting the first clamp, the second clamp having, on another side thereof, a second grip groove and a second grip expansion groove sequentially connected to each other, a grip applying a binding force to a first rod and a second rod, when the first and second clamps are connected to each other so that the first and second grip expansion grooves communicate with each other, and the first and second rods are grip-secured in the first and second grip grooves.

In some embodiments, the grip may include a first grip member having a fastening hole on one side of the first grip member and movably accommodated in the first grip expansion groove, and a second grip member including a fastening fastened to the fastening hole and a head locked at the second grip expansion groove.

In some embodiments, the first and second grip members may be fastened to the first and second clamps and rotate to apply a binding force to the first and second rods when the first and second rods are sequentially secured at the first and second clamps.

In some embodiments, the rod connector device for cervical spine may further include a fastener fastened to the first and second grip grooves of the first and second clamps and configured to confine the first and second rods, respectively.

In some embodiments, each of the first and second rods may be vertically confined by the fastener and horizontally confined by the grip.

In some embodiments, the first clamp may rotate at a predetermined angle with respect to the second clamp to adjust an angle between the first rod and the second rod.

DETAILED DESCRIPTION

Hereinafter, embodiments of the present disclosure will be described in detail. However, this is merely provided as an example, and it is to be understood that the present disclosure is not limited thereby and the present disclosure is only defined by the scope of the claims to be described below. The embodiments described below may be modified in various forms without departing from the concept and scope of the present disclosure. As far as possible, the same or similar parts are indicated using the same reference numerals in the drawings.

The terms used below is only for referring to specific embodiments and is not intended to limit the present disclosure. As used herein, singular forms also include plural forms unless the phrases clearly indicate the opposite. As used in the specification, the meaning of "comprising" or "including" specifies a specific characteristic, region, integer, step, action, element and/or component, and does not exclude the existence or addition of other specific characteristic region, integer, step, action, element and/or component.

Hereinafter, embodiments (e.g., preferred embodiments) and comparative examples of the present disclosure will be described. However, the following embodiments are only given as an embodiment of the present disclosure, and the present disclosure is not limited to the following embodiments.

Figure 4:
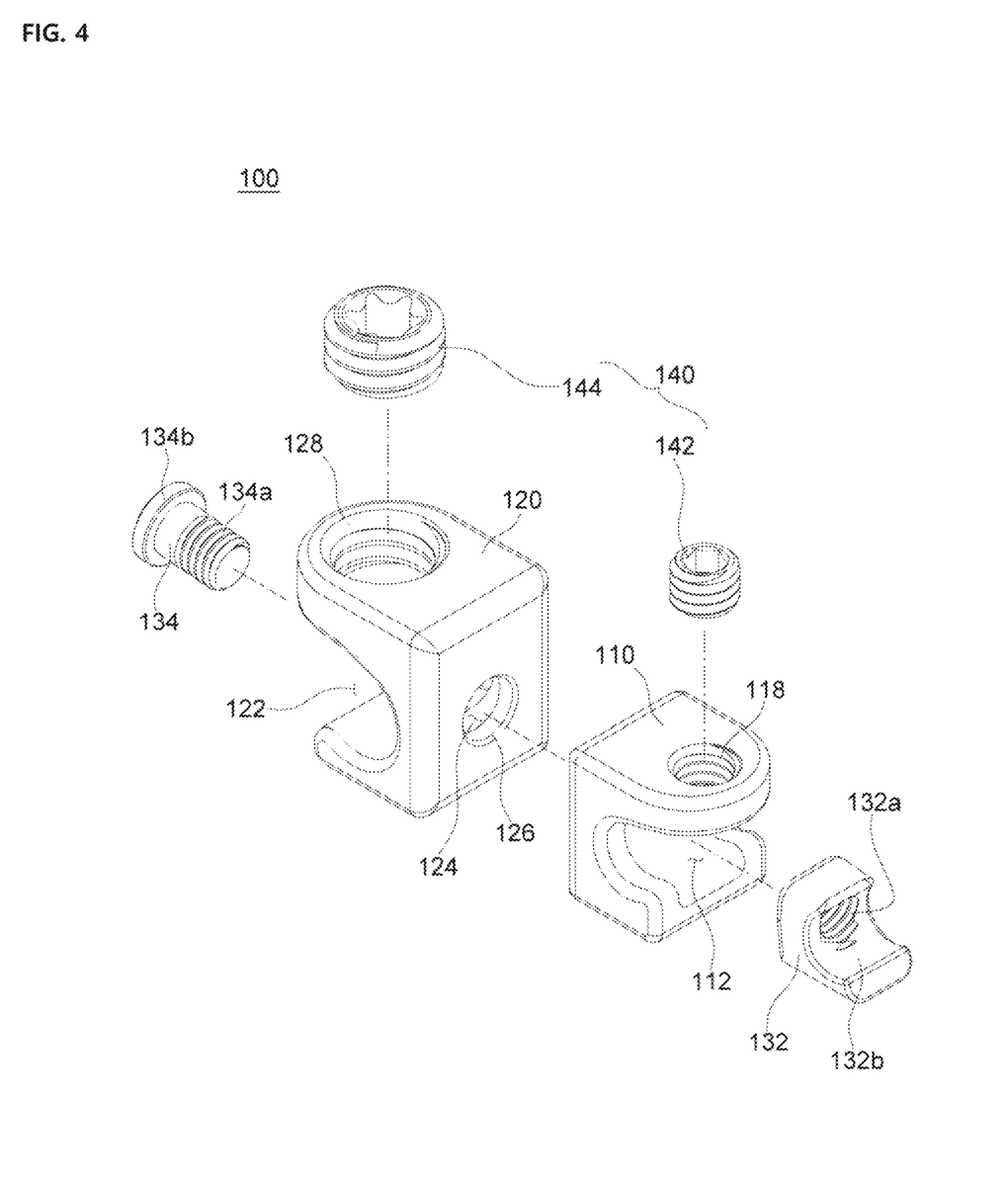
FIG. 4 is an exploded perspective view illustrating a rod connector device for cervical spine according to an embodiment of the present disclosure.
Figure 5:
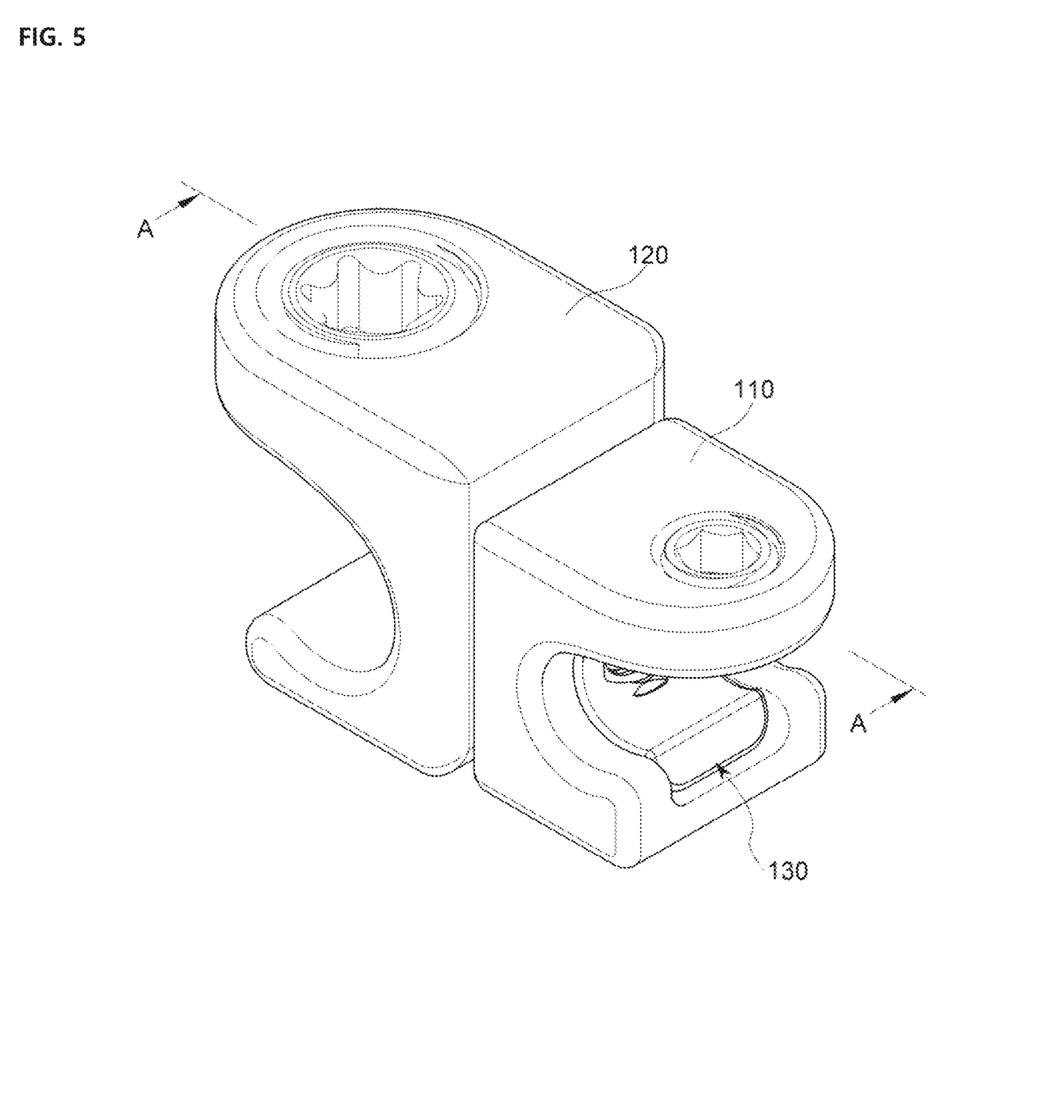
FIG. 5 is a perspective view illustrating a clamp of the rod connector device according to an embodiment of the present disclosure in a fastened state.

FIG. 4 is an exploded perspective view illustrating a rod connector device for cervical spine according to an embodiment of the present disclosure, and FIG. 5 is a perspective view illustrating a clamp of the rod connector device according to an embodiment of the present disclosure in a fastened state, As illustrated in FIGS. 4 and 5, a rod connector device 100 according to an embodiment of the present disclosure includes a first clamp 110, a second clamp 120, a grip 130 including a first grip member 132 and a second grip member 134, and a fastener 140 including a first fastening member 142 and a second fastening member 144.

In an embodiment, the rod connector device 100 is configured so that the first clamp 110 and the second clamp 120 are fastened to each other using the grip 130 in a state that the first clamp 110 and the second clamp 120 contact each other.

Figure 6:
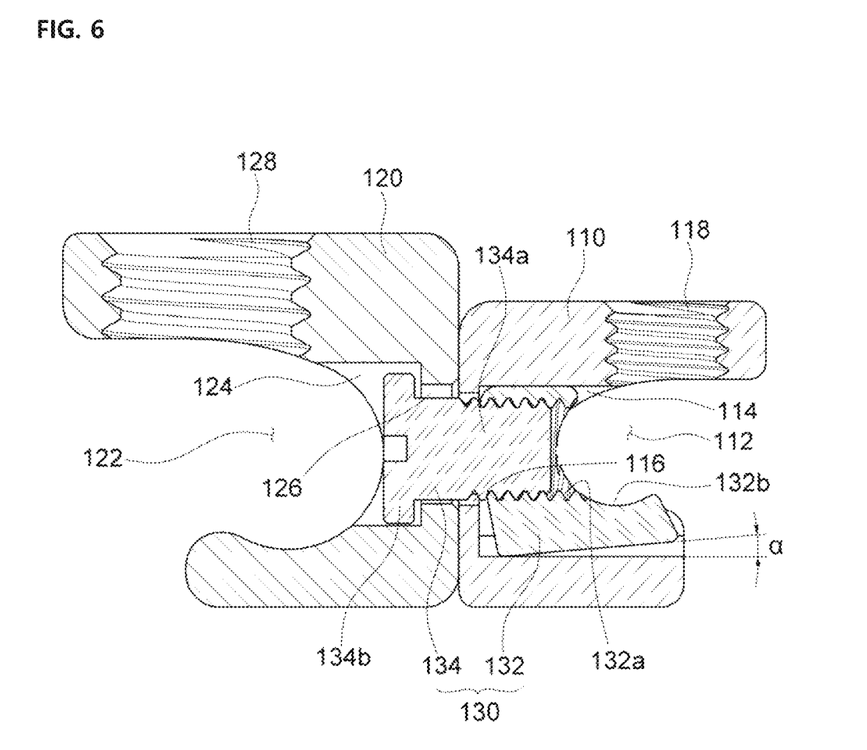
FIG. 6 is a cross-sectional view taken along line A-A of FIG. 5.

As illustrated in FIGS. 5 and 6, in the first clamp 110, a first grip groove 112 and a first grip expansion groove 114 sequentially connected to each other are defined at a side (a right side with reference to FIG. 6) of the first clamp 110, and a first through groove 116 extending from the grip expansion groove 114 is defined. In addition, a fastening hole 118 defined through to the first grip groove 112 is defined at a top portion of the first clamp 110 so as to fasten a first rod 150 to be described below.

In such an embodiment, the first grip groove 112 is a space in which the first rod 150 to be described below is fastened by the first fastening member 140 and confined. The first grip expansion groove 114 is a space in which the first grip member 132 to be described below is movably accommodated. The first through hole 116 is a through space in which the second grip member 134 to be described below is to be fastened to the first grip member 132.

As illustrated in FIGS. 5 and 6, in the second clamp 120, a second grip groove 122 and a second grip expansion groove 124 sequentially connected to each other are defined at a side (a left side with reference to FIG. 6) of the second clamp 120, and a second through groove 126 extending from the grip expansion groove 124 is defined. In addition, a fastening hole 128 defined through to the second grip groove 122 is defined at a top portion of the second clamp 120 so as to fasten a second rod 152 to be described below.

In such an embodiment, the second grip groove 122 is a space in which the second rod 152 to be described below is fastened by the second fastening member 140 and confined. The second grip expansion groove 124 is a space in which the second grip member 134 to be described below is movably accommodated. The second through hole 126 is a through space in which the second grip member 134 to be described below is to be fastened to the first grip member 132.

As illustrated in FIGS. 5 and 6, the grip 130 includes the first grip member 132 disposed in the first grip expansion groove 114 of the first clamp 110, and the second clamp member 134 disposed in the second grip expansion groove 124 of the second clamp 120. The first grip member 132 has a fastening hole 132a on one side of the first grip member 132, to which the second grip member 134 is fastened, and a hemispherical accommodation groove 132b on another side of the first grip member 132 for accommodating the first rod 150.

Figure 7:
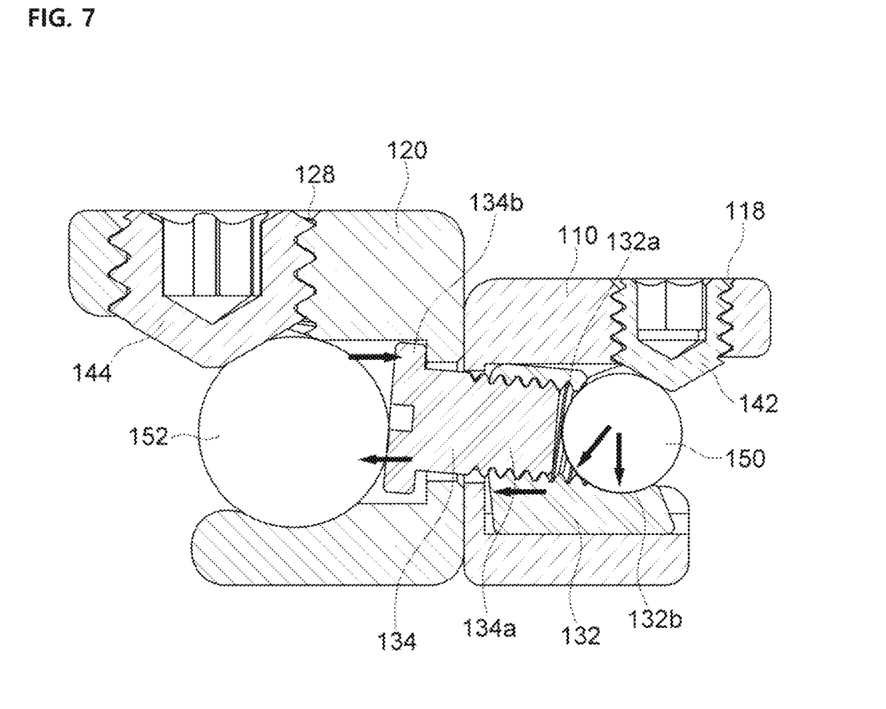
FIG. 7 is a state diagram illustrating a direction of a force applied at a rod when the rod is fastened to the rod connector device for cervical spine according to an embodiment.

In an embodiment, when the first grip member 132 is disposed in the first grip expansion groove 114 and is fastened to the second grip member 134, as illustrated in FIG. 6, an outer lower end of the first grip member 132 is lifted at a certain angle α from a bottom surface of the first grip expansion groove 114. This is to ensure that a binding force is to be applied in a horizontal direction of the first and second rods 150 and 152 when the first and second rods 150 and 152 are grip-secured. As illustrated in FIG. 7, when the first and second rods 150 and 152 are grip-secured, an entire lower end portion of the first grip member 132 contacts the bottom surface of the first grip expansion groove 114.

The second grip member 134 includes a fastening 134a to be fastened to the fastening hole 132a and a head 134b extending from the fastening 134a and to be locked at the second grip expansion groove 124.

In an embodiment, when the second grip member 134 is disposed in the second grip expansion groove 124 and is fastened to the first grip member 132, the head 134b is located horizontally (e.g., parallelly) a predetermined gap apart from the second grip expansion groove 124. On the other hand, when the first and second rods 150 and 152 are grip-secured, as illustrated in FIG. 7, the second grip member 134 is inclined at a certain angle in a clockwise direction based on the center. In such an embodiment, a lower end portion of the second grip member 134 applies a binding force in a direction of pushing the first rod 150, and an upper end portion of the second grip member 134 applies a binding force in a direction of pushing the first grip member 132.

As illustrated in FIG. 4, the fastener 140 includes the first fastening member 142 fastened vertically to the first grip groove 112 of the first clamp 110, and the second fastening member 144 fastened vertically to the second grip groove 122 of the second clamp 120.

In such an embodiment, as illustrated in FIG. 7, the first and second fastening members 142 and 144 are configured to confine the first and second rods 150 and 152 within the first and second clamps 110 and 120. That is, the first fastening member 142 is configured to confine an upper portion of the first rod 150 while the first rod 150 is seated in the accommodating groove 132b of the first grip member 132. The second fastening member 144 is configured to confine an upper portion of the second rod 152 while the second rod 152 is seated in the second grip groove 122 of the second clamp 120.

In an embodiment, the first and second fastening members 142 and 144 are in the form of a fastening without a head, and they are accommodated inside the first and second fastening holes 118 and 128 when fastened.

Figure 9:
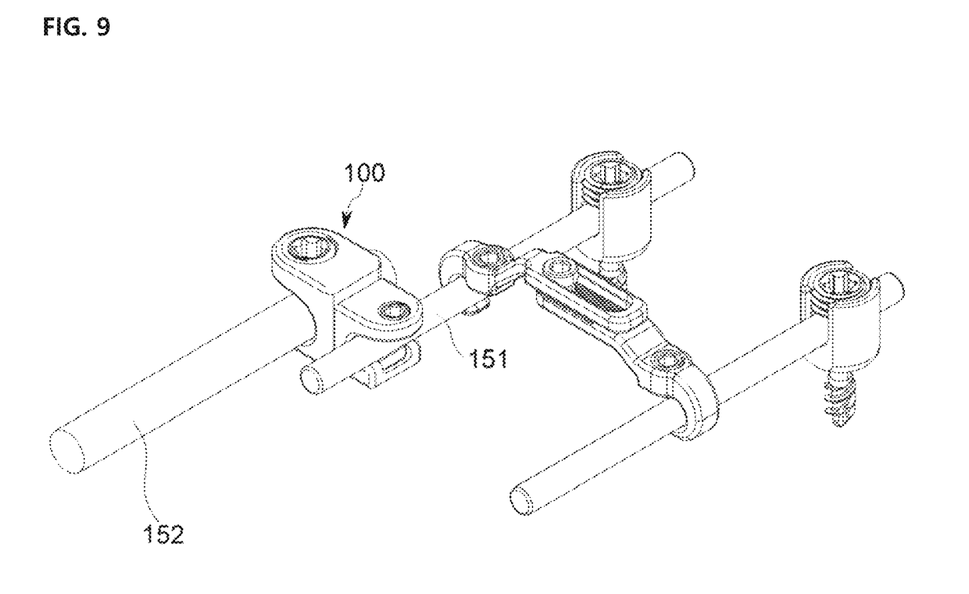
FIG. 9 is a view illustrating a state of use in which the rod connector device is fastened to the securing device for cervical spine according to an embodiment.

In an embodiment, as illustrated in FIG. 9, the first rods 150 are arranged as a pair of cervical rods in a length direction of a cervical spine. The second rod 152 is a spinal rod and is arranged to be outside of the cervical rod. It is obvious that the second rod 152 may be disposed inwardly of the first rod 150.

Accordingly, the rod connector device 100 may be used to extend the second rod 152 with respect to the first rod 150 in the length direction.

Hereinafter, a process of assembling the first and second clamps and the first and second grip members of the rod connector device for cervical spine and a process of applying the binding force in the assembled state will be described with reference to FIGS. 5 to 8.

First, as illustrated in FIG. 5, the first clamp 110 and the second clamp 120 are connected to each other using the first and second grips 130 and 132. In such an embodiment, as illustrated in FIG. 6, the first grip member 132 is disposed so that one lower end is lifted at a certain angle α from the bottom surface of the first grip expansion groove 114 and is inclined. On the other hand, the second grip member 134 is disposed horizontally (parallelly) in the second grip expansion groove 124. Next, as illustrated in FIG. 7, when the first rod 150 is fastened to the first clamp 110 using the first fastening member 142, a binding force is vertically applied to the first rod 150 through the first fastening member 142, and the binding force is delivered to the first and second grip members 132 and 134 by the first rod 150, and from the first and second grip members 132 and 134 to the second rod 152. In such an embodiment, an entire bottom surface of the first grip member 132 contacts the first grip expansion groove 114. On the other hand, the fastening 134a of the second grip member 134 is inclined in a clockwise direction such that the head 132b contacts an upper end portion of the second grip expansion groove 124.

Lastly, when the second rod 152 is fastened to the second clamp 120 using the second fastening member 144, a horizontal binding force is applied by the second rod 152 and is sequentially delivered to the second grip member 134 and the first grip member 132.

Accordingly, the first and second rods 150 and 152 are vertically confined by the first and second fastening members 142 and 144 and horizontally confined by the first and second grip members 132 and 134 in the first and second clamps 110 and 120, respectively.

Figure 8:
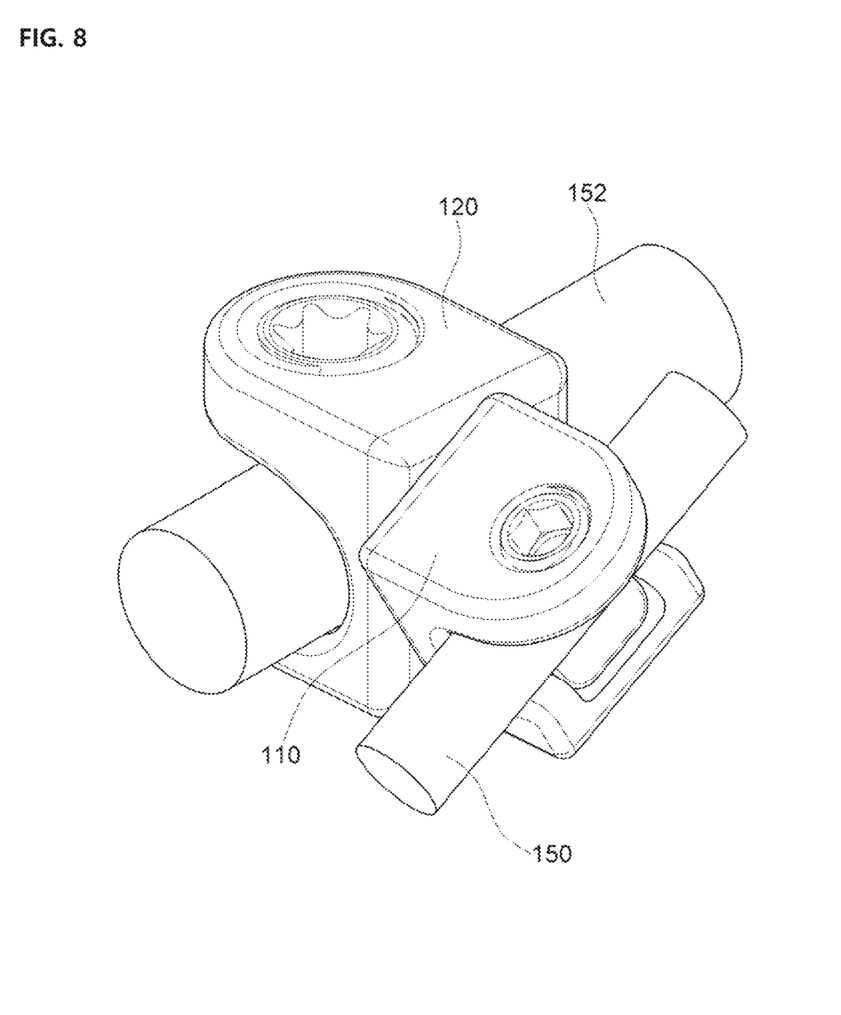
FIG. 8 is a view illustrating a state in which a rod is fastened to the rod connector device for cervical spine according to an embodiment.

In an embodiment, even in a state that the first and second rods 150 and 152 are confined in vertical and horizontal directions by the first and second fastening members 142 and 144 and the first and second grip members 132 and 134, as illustrated in FIG. 8, the first clamp 110 may rotate in a counterclockwise direction with respect to the second clamp 120. This is because the fastening 134a of the second grip member 134 is right-screwed into the fastening hole 132a of the first grip member 132, and when the first clamp 132 rotates in the counterclockwise direction, the binding force may be partially released in a horizontal direction.

On the other hand, when the fastening 134a of the second grip member 134 is left-screwed to the fastening hole 132a of the first grip member 132, the first clamp 110 may rotate in a clockwise direction with respect to the second clamp 120s.

The rod connector device for cervical spine according to an embodiment of the present disclosure allows the first clamp 110 to rotate with respect to the second clamp 120 at a predetermined angle, and thus the rod connector device may be installed while adjusting an angle between the first rod 150 and the second rod 152 in an operation they should not be connected in parallel to each other.

As set forth hereinabove, in a rod connector device for cervical spine according to one or more embodiments of the present disclosure, the first clamp may rotate at a predetermined angle with respect to the second clamp, and accordingly, the rod connector may be conveniently installed while conveniently adjusting the angle between the first rod and the second rod.

In addition, the rod connector device for the cervical spine according to one or more embodiments of the present disclosure may be universally applicable irrespective of the position of the rod installed on the cervical spine during surgery.

Although the embodiments of the present disclosure have been illustrated and described as above, various modifications and other embodiments may be made by those skilled in the art. These modifications and other embodiments are all considered and included in the appended claims and will not depart from the true spirit and scope of the present disclosure.

What is claimed is:

1. A rod connector device for cervical spine, comprising:
   a first clamp having, on one side thereof, a first grip groove and a first grip expansion groove sequentially connected to each other;
   a second clamp contacting the first clamp, the second clamp having, on another side thereof, a second grip groove and a second grip expansion groove sequentially connected to each other;
   a grip applying a binding force to a first rod and a second rod, when the first and second clamps are connected to each other so that the first and second grip expansion grooves communicate with each other, and the first and second rods are grip-secured in the first and second grip grooves,
   wherein the grip comprises:
   a first grip member having a fastening hole on one side of the first grip member and movably accommodated in the first grip expansion groove, and
   a second grip member including a fastening fastened to the fastening hole and a head locked at the second grip expansion groove,
   wherein the first grip member is configured to be movable so as to be inclined at a predetermined angle with respect to a bottom surface of the first grip expansion groove.

2. The rod connector device for cervical spine of claim 1, wherein the first and second grip members are fastened to the first and second clamps and rotate to apply a binding force to the first and second rods when the first and second rods are sequentially secured at the first and second clamps.

3. The rod connector device for cervical spine of claim 1, further comprising a first fastener fastened to the first grip groove of the first clamp and a second fastener fastened to the second grip groove of the second clamp and configured to confine the first and second rods, respectively.

4. The rod connector device for cervical spine of claim 3, wherein each of the first and second rods is vertically confined by the first fastener and the second fastener, respectively, and horizontally confined by the grip.

5. The rod connector device for cervical spine of claim 3, wherein the first clamp rotates at a predetermined angle with respect to the second clamp to adjust an angle between the first rod and the second rod.

\* \* \* \* \*